United States Patent [19]

Spiegel

[11] Patent Number: 5,712,262

[45] Date of Patent: Jan. 27, 1998

[54] USE OF SPHINGOSINE-1-PHOSPHATE TO SUPPRESS PROGRAMMED CELL DEATH

[76] Inventor: Sarah Spiegel, 6343 Linway Terr., McLean, Va. 22101

[21] Appl. No.: 754,323

[22] Filed: Nov. 21, 1996

[51] Int. Cl.$^6$ .................................................. A61K 31/66
[52] U.S. Cl. ......................................................... 514/114
[58] Field of Search ............................................. 514/114

[56] References Cited

PUBLICATIONS

Ohta et al., FEBS Letters (1994), 355(3), 267–70.

Primary Examiner—Phyllis G. Spivack
Attorney, Agent, or Firm—Glenna Hendricks; Carol Carr

[57] ABSTRACT

Admisistration of sphingosine-1-phosphate to retard apoptosis in degenerative diseases as neurodegenerative disease, ischemic stroke and aging is disclosed wherein slowing of the process of programmed cell death is useful as a means to slow the degenerative process in patients suffering from these diseases.

5 Claims, No Drawings

USE OF SPHINGOSINE-1-PHOSPHATE TO SUPPRESS PROGRAMMED CELL DEATH

This application is a continuation-in-part of Provisional Patent Application 60/007,396 filed Nov. 21, 1995 and takes priority therefrom.

FIELD OF THE INVENTION

This invention is related to methods of retarding apoptosis in degenerative diseases such as neurodegenerative disease, ischemic stroke and aging wherein slowing of the process of programmed cell death is useful as means to slow the degenerative process in patients suffering from degenerative diseases by administration of sphingosine-1-phosphate (SPP), esters, phosphonates and analogues of SPP to the affected tissue.

BACKGROUND OF THE INVENTION

The sphingolipid metabolites, sphingosine, sphingosine-1-phosphate (SPP) and sphingosylphosphorylcholine (SPC) are emerging as a new class of intracellular second messengers with a wide spectrum of activity in cell growth regulation and signal transduction. It is known that ceramide is an important regulatory participant in programmed cell death (apoptosis) induced by tumor-necrosis factor-$\alpha$ (TNF$\alpha$) and Fas ligand, members of the TNF superfamily. Conversely sphingosine and sphingosine-1-phosphate (SPP), which are metabolites of ceramide, induce mitogenesis and have been implicated as second messengers in cellular proliferation induced by platelet-derived growth factor and serum.

The use of SPP to inhibit cell motility and chemoinvasive motility in cancer cells is taught in U.S. Pat. Nos. 5,391,800 and 5,260,288 to Igarashi, et al. These patents are incorporated herein by reference in their entirety. However, those patents do not teach use of SPP to delay programmed cell death.

U.S. Pat. Nos. 5,194,654 and 5,463,092 to Hostetler and Kumar (both of which are incorporated herein in their entirety by reference) teach liposomes containing lipid derivatives of phosphonacids, including sphingolipids, as antiviral compositions. There is no teaching therein regarding use of any composition to inhibit apoptosis.

DETAILED DESCRIPTION OF THE INVENTION

It is the purpose of this invention to provide means of delaying programmed cell death in patients suffering from degenerative diseases by administration of sphingosine-1-phosphate (SPP), esters, thioesters and phosphonates of SPP to the affected tissue. It is a further purpose of this invention to delay signs of aging, particularly in epidermal tissue, by application of compositions containing sphingosine-1-phosphate in new compositions wherein the active agent is provided on solid supports. Hence, the invention provides method of delaying programmed cell death by administration of a programmed cell death-delaying effective amount of sphingosine-1-phosphate. The compositions containing sphingosine-1-phosphate may be administered directly to the cells or parenterally to obtain a concentration of 0.1 µM to 100 µM in the affected tissue. Preferred concentration is 2 µM to 10 µM. For example, the compositions for injection include sterile distilled water, saline, glucose, and so forth. For topical application, compositions useful for injection may be used. However, other carriers usually used in pharmaceuticals for topical composition may be used to deliver medicaments in forms such as gels, lotions, foams and sprays. Compositions containing SPP may be administered on solid supports, including bandages and applicators which are impregnated with the SPP. Additionally, it is possible to apply compositions such as solutions or gels containing SPP with solid, non-absorbent applicators such as plastic or glass rods. Such non-absorbent applicators may be conveniently attached to the closing means of a container which contains SPP in a carrier. SPP may also be administered in a cyclodextrin inclusion complexes as a powder or a lozenge. SPP may be administered in conjunction with other active agents such as antibiotics or anti-inflammatory agents. For such applications salves, gels or lotions may be particularly useful. It is also possible to administer the active agents in liposomes made by known methods such as those of Hostetler as taught in U.S. Pat. No. 5,194,654, which is incorporated herein by reference in its entirety as though fully reproduced herein.

The phosphates can, for example, be made in accord with the teaching of Igarashi, et al, U.S. Pat. No. 5,391,800, which has been incorporated herein by reference in its entirety as though fully reproduced herein.

SPP may also be applied as a spray to the target tissue. SPP may be administered to other epithelial tissue such as the rectum or vagina in the form of suppositories, retention enemas or as douches.

Sphingosine-1-phosphate (SPP) prevents the appearance of the key features of apoptosis, namely, intranucleosomal DNA fragmentation and morphological changes, which result from increased concentrations of ceramide. Furthermore, inhibition of ceramide-mediated apoptosis by activation of protein kinase C results from stimulation of sphingosine kinase and the concomitant increase in intracellular sphingosine-1-phosphate. Finally, sphingosine-1-phosphate not only stimulates the extracellular signal-regulated kinase (ERK) pathway, but also counteracts the ceramide-induced activation of stress-activated protein kinase. Thus, the balance between the intracellular levels of ceramide and sphingosine,1-phosphate and their regulatory effects on different family members of mitogen-activated protein kinases determines the fate of the cell.

Materials and Methods

Inhibition by SPP of apoptosis induced by N-acetyl sphingosine or with sphingomyelinase (SMase):

Logarithmically growing HL-60 cells ($1 \times 10^6$ ml$^{-1}$) were incubated in serum-free RPMI 1640 supplemented with insulin (5 mgl$^{-1}$) and treated with vehicle alone or SPP (obtained from Biomol) added as a BSA complex in the absence or presence of an apoptotic agent in varying samples.

Cells were treated with 10 µM $C_2$-ceramide (Biomol) for 6 hours, then lysed and their nucleic acids analyzed by electrophoresis on a 1.8% agarose gel stained with ethidium bromide.

Duplicate cultures were incubated with or without 10 µM $C_2$ ceramide in the absence or presence of 10 µM SPP.

Tests were repeated using U937 cells incubated in serum-free medium with and without 100 mU ml$^{-1}$ *Staphylococcus aureus* sphingomyelinase (Sigma) in the presence of vehicle or SPP and chromosomal DNA fragmentation was assessed by agarose gel electrophoresis.

Apoptotic cells were detected by in situ staining using a TACS-1 kit obtained from Trevigen, which gives a dark brown insoluble precipitate indicative of genomic fragmentation.

In further studies, HL-60 cells were incubated with [$^3$H] thymidine (1 μCi ml$^{-1}$) for 24 hours to label DNA, then washed before exposure to various agents [(1) SMase only, (2) SMase+SPP (10 μM) or (3) SPP (10 μM) only ] for four hours. Cells were lysed and [$^3$H]thymidine incorporated into both soluble and unfragmented DNA was determined by liquid scintillation counting.

Results

Consistent with previous studies, increasing intracellular levels of ceramide in human promyelocytic HL-60 cells or U937 monoblastic leukemia cells either by addition of membrane-permeable ceramide analogue $C_2$-ceramide or by treatment with sphingomyelinase induced apoptosis. Exposure to sphingosine-1-phosphate prevented ceramide-induced apoptosis in both cells lines as measured by oligonucleosomal DNA fragment electrophoresis and by a qualitative DNA fragment assay. SPP also markedly reduced genomic fragmentation and the morphological changes associated with apoptosis, as detected by in situ staining.

It was also shown that SPP reduced TNF-induced DNA strand breaks and the expression of the apoptotic traits. I addition, SPP inhibited apoptosis induced by Fas ligation in Fas-expressing Jurkat T cells.

Without relying on any particular theory of mechanism, it is instructive that activation of protein kinase C antagonizes apoptosis induced by TNF-α, Fas ligand and ionizing radiation, suggesting that the diacylglycerol/protein kinase C pathway counteracts ceramide-mediated apoptosis. Moreover, inhibitors of protein kinase C induce apoptosis in hematopoietic and neoplastic cell lines. Although the mechanism by which protein kinase C opposes ceramide-mediated apoptosis has not been determined, activation of this enzyme in diverse cell types stimulates sphingosine kinase activity resulting in intracellular accumulation of SPP.

It was seen that SPP prevented apoptosis induced by several inhibitors of protein kinase C, including the bisindolylmaleimide GF109230X, H7, calphostin C, UCN-01 (7-hydroxystaurosporine), and chelerythrin in Swiss 3T3 and U937 cells.

In order to verify that the activation of the sphingosine kinase by protein kinase C was responsible for inhibiting ceramidemediated apoptosis, a competitive inhibitor of sphingosine kinase, N,N-dimethylsphingosine, which is a more potent inhibitor of sphingosine kinase than of protein kinase C was also used. Activity of protein kinase C by TPA stimulated sphingosine kinase and increased SPP in both U937 cells and Jurkat T cells. Interestingly, the amount of SPP in cells exposed to TPA was similar to that in cells treated with a cytoprotective concentration (1 μM) of SPP.

Example 1

To 15 ml of phosphate buffered saline (PBS) is added 3 mg of sphingosine-1-phosphate. The composition is placed in a bottle having a stopper with a smooth glass rod extending into the solution. The composition is applied to decubitus ulcers using the smooth glass rod as an applicator. The composition may also be administered as a spray from a bottle with an atomizer.

Example 2

To a 4×4 inch sponge there is applied to the smooth surface 0.02 ml of the solution prepared as a 2 μM solution in PBS. The prepared bandage is then enclosed in a foil covering which is made air-tight. For application, the bandage is unwrapped and is applied smooth side down on the wound.

Example 3

A composition is prepared for use on the skin or mucosa in the following manner:

| Ingredient | % w/w |
| --- | --- |
| SPP | 0.5% |
| propylene glycol | 13.0% |
| Phosphate buffered saline | 86.5% |

When the active agent is administered to the mucosa of the oral cavity, it may be administered as a buccal tablet or as a spray for use in the oral-pharyngeal cavity and the nasal cavities.

Example 4

A composition prepared as a gel for application to the skin:

| Ingredient | % w/w |
| --- | --- |
| the methylthio ester of SPP | 0.5% |
| propylene glycol | 10.0% |
| Polyethylene glycol | 89.5% |

Example 5

A composition prepared for administration as a suppository:

| Ingredient | % w/w |
| --- | --- |
| the propyl ester of SPP | 0.5 mg |
| glyceryl monosterate | 1.0 Gm |
| hydrogenated coconut oil | 1.0 Gm |
| glyceryl monopalmitate | 1.0 Gm |

Example 6

A patch composed of trilaminate of an adhesive matrix sandwiched between a non-permeable backing and a protective covering layer is prepared in the following manner:

To a pressure-sensitive silicone adhesive composition BIOPSA™ Q7-2920 (Dow Corning Corp., Midland, Mich., U.S.A.) in cyclohexane (50% w/v) is added sufficient SPP to provide a 0.5% SPP composition. The adhesive is applied to a polyester film to provide in successive layers to provide about 2 mg of active agent per cm$^2$. The film containing the adhesive is then made into patches of 10 cm$^2$. Patches would be covered with a protective layer to be removed before application of the patch. Patches may be prepared containing permeation enhancers such as cyclodextrin, butylated hydroxyanisole, or butylated hydroxytoluene.

A spray or mist containing SPP would be appropriate for application to the skin. Preservatives and coloring agents may also be added. The spray may simply be formed by an atomizer on the container, it is not necessary to use a special carrier to enhance vaporization, though use of a vehicle to enhance vaporization is not precluded. It is also possible to deliver compositions containing the active agent using a smooth solid support such as a smooth glass or plastic rod.

Compositions of the invention may also be applied using vehicles such as oils, alcohols, DMSO and such to carry the active agent across the skin barrier. Sphingosine-1-phosphate may be added to cosmetics as a means of delaying aging of the skin.

What I claim is:

1. A method of delaying programmed cell death by administration of a programmed cell death-delaying effective amount of sphingosine-1-phosphate.

2. A method of claim 1 wherein the sphingosine-1-phosphate is administered in a pharmaceutically acceptable carrier.

3. A method of claim 1 wherein the sphingosine-1-phosphate is administered in a cosmetic.

4. A method of claim 1 wherein the sphingosine-1-phosphate is administered by parenteral means.

5. A method of claim 1 wherein the sphingosine-1-phosphate is administered in a cream, lotion, gel or salve.

* * * * *